(12) United States Patent
Ogura

(10) Patent No.: US 6,172,240 B1
(45) Date of Patent: Jan. 9, 2001

(54) PYRROLE DERIVATIVES, FILM-FORMING MATERIAL AND METHOD OF PREPARING THE DERIVATIVES

(75) Inventor: Katsuyuki Ogura, Narashino (JP)

(73) Assignee: Chiba University, Chiba (JP)

( * ) Notice: Under 35 U.S.C. 154(b), the term of this patent shall be extended for 0 days.

(21) Appl. No.: 09/473,883

(22) Filed: Dec. 29, 1999

(30) Foreign Application Priority Data

Mar. 5, 1999 (JP) .................................................. 11-057838

(51) Int. Cl.⁷ ........................ C07C 255/09; C07D 409/14
(52) U.S. Cl. ........................ 548/527; 558/432; 558/370; 160/287.2; 160/287.3; 160/287.32
(58) Field of Search .......................... 548/527; 558/370, 558/432; 160/287.2, 287.3, 287.32

(56) References Cited

PUBLICATIONS

Meeker et al., Macromolecules (1998), 31(9) pp. 2943–2946.*

* cited by examiner

*Primary Examiner*—Joseph K. McKane
*Assistant Examiner*—Taofiq A. Solola
(74) *Attorney, Agent, or Firm*—Sughrue, Mion, Zinn, Macpeak & Seas, PLLC

(57) ABSTRACT

The present invention relates to pyrrole derivatives, particularly 2-(2-thienyl)-5-(5-tricyanoethenyl-2-thienyl)pyrrole derivatives, which has metallic luster, good stability in air, and a high solubility in an organic solvent, and which is suitable for a film-forming material.

18 Claims, 3 Drawing Sheets

(3 of 3 Drawing Sheet(s) Filed in Color)

PYRROLE DERIVATIVES, FILM-FORMING MATERIAL AND METHOD OF PREPARING THE DERIVATIVES

BACKGROUND OF THE INVENTION

1. Field of the Invention

This invention relates to metallically-lustered pyrrole derivatives, particularly 2-(2-thienyl)-5-(5-tricyanoethenyl-2-thienyl)pyrrole derivatives, which can be used for a coating material, organic metal plating material, organic semiconductor material or the like.

2. Description of Related Art

It has been known that a high-molecular weight compound having a conjugated π-electron system in the molecule thereof has a metallic luster. Because the metallic luster in such a compound is based on free electrons in the π-electron system, the compound is expected to have semiconductor-like properties. Poly(acetylene), poly(sulfur nitride) and the like are examples of such a compound.

SUMMARY OF THE INVENTION

Since they are unstable in doped and even undoped states, organic compounds having metallic luster which are stable even in air are demanded.

Further, since the high-molecular weight compound having a π-electron conjugated system generally has a low solubility in an organic solvent, it is difficult to form a film by dissolving the compound in the organic solvent to make a solution and then applying the resulting solution on an appropriate substrate.

An object of the invention is, therefore, to provide an organic compound which has metallic luster and is stable even in air.

Further, another object of the invention is to provide the organic compound which has a high solubility in the organic solvent and consequently is an excellent film-forming material.

There is, therefore, a provision of pyrrole derivatives, particularly 2-(2-thienyl)-5-(5-tricyanoethenyl-2-thienyl) pyrrole derivatives, having the following general formula:

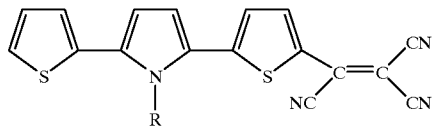

(R represents hydrogen, a substituted or unsubstituted alkyl group, a substituted or unsubstituted aromatic group, formyl group, an acyl group, an alkoxycarbonyl group, or an alkenyl group.)

Moreover, there is a provision of a film-forming material composed of the above pyrrole derivative, and further provision of the present invention is a method of preparing the above derivatives.

As mentioned above, some high-molecular weight compounds have been known which have metallic luster. However, no organic low-molecular weight compound has been reported at all which clearly has metallic luster.

The inventor has found that the aforementioned low-molecular weight compound which has the specific structure, namely the π-electron conjugated system, in a molecule thereof has a stable metallic luster and good stability in air, and further has a high solubility in common organic solvents and hence is an excellent film-forming material, and then accomplished this invention.

The aforementioned compounds having the tricyanoethenyl group show a clear gold color, bronze color or the like in its crystal state or thin film state. Further, nevertheless the compounds can dissolve in the common organic solvents such as acetone, benzene, chloroform, or the like, they can easily precipitate therefrom after dissolving therein. For example, standing of the solution allows metallic colored crystals to precipitate therefrom.

Further, by developing, coating, and drying the solution containing the compound in the organic solvent on a surface of an appropriate substrate, a coating film can easily be formed thereon.

Since the compounds according to the present invention have a surprisingly high stability against beat, they can be used for formation of a evaporated film. Further, by heating the compound up to not less than its melting point to melt it and then cooling the melt, crystals can be formed. Moreover, the compounds according to the invention can have a stable melting state and also exhibit a relatively high electrical conductivity.

Besides, iodine or the like may dope into the compound according to the present invention, for the purpose of enhancing its electrical conductivity.

In the aforementioned general formula, R represents hydrogen, a substituted or unsubstituted alkyl or cycloalkyl group, a substituted or unsubstituted aromatic group, formyl group, an acyl group, an alkoxycarbonyl group, or an alkenyl group. Besides, the alkyl or cycloalkyl group constituting R preferably has 1–18 carbon(s) and more preferably 1–12 carbon(s). The substituent for the an alkyl or cycloalkyl group is preferably alkoxy group having 1–18 carbon(s); an aromatic group such as phenyl group, naphthyl group, benzothienyl group, indolyl group, pyridyl group, phenoxy group, naphthyloxy group; or a halogen atom such as bromine, iodine, chlorine, or fluorine.

The aromatic group constituting R is preferably phenyl group, naphthyl group, thienyl group, benzothienyl group, indolyl group, pyridyl group or the like. A substituent for the aromatic group is preferably alkyl group having 1–18 carbon(s), more preferable 1–12 carbon(s), alkoxy group having 1–18 carbon(s), more preferable 1–12 carbon(s), phenoxy group, naphthyloxy group, monoalkylamino group, dialkylamino group, thioalkyl group, bromine, iodine, chlorine, fluorine. An alkyl group constituting the monoalkylamino group, the dialkylamino group, or the thioalkyl group has preferably 1–18 carbon(s).

The acyl group, the alkoxycarbonyl group, or the alkenyl group constituting R preferably has 1–18 carbon(s), more preferable 1–12 carbon(s).

Particularly when R represents alkylphenyl or alkoxyphenyl group having 4–12 carbons of alkyl or alkoxy group, a thin film with metallic luster can be made by spin coating the compound according to the invention on the appropriate substrate.

The compound according to the invention can be manufactured by reacting a compound shown by the following general formula with tetracyanoethylene in an organic solvent.

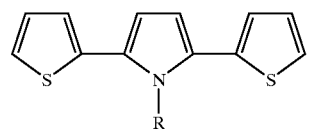

Alternatively, an organic metal compound shown by the following general formula is produced by reacting the above compound with a base such as butyllithium, lithium diisopropylamide or the like.

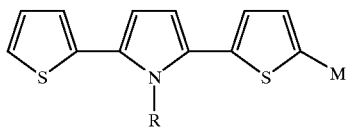

Subsequently, the reaction of the resulting compound with tetracyanoethylene generates the compound according to the invention.

Besides, when R is t-butoxycarbonyl group, heating of the compound according to the invention can bring substitution of R by hydrogen.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DESCRIPTION OF THE PREFERRED EMBODIMENTS

The present invention will be explained in detail below with reference to Examples, but it does not intend to limit the present invention.

EXAMPLE 1

Figure 1:
FIG. 1 is a photograph showing the crystals of the compound in Example 1, 1-[(4-n-hexyloxy)phenyl]-2-(2-thienyl)-5-(5-tricyanoethenyl-2-thienyl)pyrrole.

After dissolving 1-[(4-n-hexyloxy)phenyl]-2,5-bis(2-thienyl)pyrrole (205 mg) into N,N-dimetylformamide (30 ml), tetracyanoethylene (126 mg) was added thereto, and then they were stirred for 24 hours at room temperature. After addition of water thereinto, extraction by toluene was conducted. The obtained organic layer is dried over anhydrous sodium sulfate, and then condensation thereof under vacuum was conducted. Subsequently, the condensed substance is separated by silica gel column chromatography using toluene as eluent to obtain 1-[(4-n-hexyloxy)phenyl]-2-(2-thienyl)-5-(5-tricyanoethenyl- 2-thienyl)pyrrole (212 mg, yield 83%). After recrystallization from a chloroform-hexane mixture solvent, crystals having a bronzy metallic luster were obtained. FIG. 1 is a photograph showing the appearance of the crystals. Further, physical properties thereabout are shown bellow.

m.p.: 215.2–216.5° C.

$^1$H NMR (CDCl$_3$, 300 MHz): δ0.94(3H, t, J=7.0 Hz), 1.35–1.54(6H, m), 1.85(2H, tt, J=7.1 Hz), 4.06(2H, t, J=6.5 Hz), 6.74(1H, d, J=4.4 Hz), 6.86(1H, dd, J=1.1 and 3.8 Hz), 6.90(dd, 1H, J=3.8 and 5.0 Hz), 7.07(d, 1H, J=4.4 Hz), 7.07(d, 2H, J=8.8 Hz), 7.08(d, 1H, J=4.5 Hz), 7.17(dd, 1H, J=1.1 and 5.0 Hz), 7.29(d, 2H, J=8.9 Hz), 7.73(d, 1H, J=4.7 Hz)

Infrared absorption spectrum (KBr):
2363, 2215, 1655, 1560, 1491, 1362, 1252, 1182 cm$^{-1}$ Ultraviolet-visible absorption spectrum (THF):
λmax (ε/M$^{-1}$cm$^{-1}$): 328 nm (14000), 624 nm (41000)

EXAMPLE 2

A solution of 1-(2-isopropyl)-2,5-di(2-thienyl)pyrrole (240 mg, 0.878 mmol) in THF was cooled to −78° C. under nitrogen atmosphere, and then n-butyl lithium (0.6 ml, 1.5M, 0.9 mmol) was dropped thereinto, and subsequently they were stirred for 15 minutes. The obtained solution was dropped into a solution of tetracyanoetylene (342 mg, 1.25 mmol) in THF solution (50 ml) at −78° C., and then they were stirred for 15 minutes. The reaction solution was warmed up to room temperature and stirred for 30 minutes. Then addition of a saturated ammonium chloride aqueous solution (10 ml) thereto stopped the reaction thereon. Further, water (100 ml) was added thereinto, and then three times of extractions by 100 ml of chloroform at each time were conducted. The obtained organic layer was dried by anhydrous sodium sulfate, and then condensation thereof under vacuum was conducted. Subsequently, the condensed substance was separated by a mixture solution (chloroform-bexane=5:1) as eluent in silica gel column chromatography to obtain 1-(2-isopropyl)-2-(2-thienyl)-5-(5-tricyanoethenyl-2-thienyl)pyrrole (219 mg, 0.584 mmol, yield 67%) in crystal state, the crystals had a gold color. Physicochemical properties thereabout are shown bellow.

m.p.: 179.0–180.0° C.

$^1$H NMR (CDCl$_3$, 300 MHz): δ1.50 (d, 6H, J=7.0 Hz), 4.83 (septet, 1H, J=7.0 Hz), 6.35(d, 1H, J=4.0 Hz), 6.67(d, 1H, J=4.0 Hz), 7.11(dd, 1H, J=3.6 and 5.1 Hz), 7.44(dd, 1H, J=1.4 and 3.6 Hz), 7.27(d, 1H, J=4.4 Hz), 7.44(dd, 1H, J=1.4 and 5.1 Hz), 8.03(d, 1H, J=4.4 Hz)

Infrared absorption spectrum (KBr):
2210, 1500, 1450, 1430, 1405, 1380, 1355, 1290, 1178, 1105 cm$^{-1}$ Ultraviolet-visible absorption spectrum (THF):
λmax (ε/M-1 cm$^{-1}$): 585 nm (39500)

EXAMPLES 3–35

Figure 2:
FIG. 2 is a photograph showing the crystals of the compound in Example 20, 1-(2-bromophenyl)-2-(2-thienyl)-5-(5-tricyanoethenyl-2-thienyl)pyrrole.

A compound in each Example shown in FIGS. 1 and 2 was manufactured in the same procedures as Example 1 or 2, and a melting point, appearances, $^1$H NMR, and an ultraviolet-visible absorption spectrum thereabout were measured. Among them, Tables 1 and 2 show each substituent R, m.p. and appearances.

TABLE 1

| Example No. | R | m.p. (° C.) | appearance |
|---|---|---|---|
| 3 | p-CH$_3$O—C$_6$H$_4$ | 219.6–220.4 | bronzy crystal |
| 4 | p-C$_2$H$_5$O—C$_6$H$_4$ | 201.5–202.4 | yellowish gold crystal |
| 5 | p-n-C$_4$H$_9$O—C$_6$H$_4$ | 174.5–175.3 | bronzy crystal |
| 6 | p-n-C$_{12}$H$_{25}$O—C$_6$H$_4$ | 153.2–153.6 | brown crystal |
| 7 | p-CH$_3$—C$_6$H$_4$ | 222–222.5 | gold crystal |
| 8 | m-CH$_3$—C$_6$H$_4$ | 213.5–214 | gold crystal |
| 9 | p-n-C$_4$H$_9$—C$_6$H$_4$ | 171.5–172.5 | bronzy crystal |
| 10 | p-tert-C$_4$H$_9$—C$_6$H$_4$ | 235.5–236 | gold crystal |
| 11 | p-sec-C$_4$H$_9$—C$_6$H$_4$ | 188–189 | dull greenish gold crystal |
| 12 | p-n-C$_6$H$_{13}$—C$_6$H$_4$ | 156–157 | bronzy crystal |
| 13 | p-n-C$_{12}$H$_{25}$—C$_6$H$_4$ | 138–139 | magenta powder |
| 14 | CH$_3$ | 209–210 | gold crystal |
| 15 | cyclohexyl | 186.5–187 | auburn crystal |
| 16 | p-F-C$_6$H$_4$ | 246.2–247 | gold crystal |
| 17 | m-F-C$_6$H$_4$ | 241.5–242.5 | greenish gold crystal |
| 18 | o-F-C$_6$H$_4$ | 225–226 | greenish gold crystal |

TABLE 2

| Example No. | R | m.p. (° C.) | appearance |
|---|---|---|---|
| 19 | m-Br—$C_6H_4$ | 258–259.5 | deep greenish gold crystal |
| 20 | o-Br—$C_6H_4$ | 202–202.5 | gold crystal |
| 21 | p-Cl—$C_6H_4$ | 245–245.8 | gold crystal |
| 22 | m-Cl—$C_6H_4$ | 247.5–248.5 | greenish gold crystal |
| 23 | o-Cl—$C_6H_4$ | 188–189 | greenish gold crystal |
| 24 | m-I—$C_6H_4$ | 239.2–240 | brownish gold crystal |
| 25 | p-$Me_2$N—$C_6H_4$ | 252–253 | magenta powder |
| 26 | p-tert-$C_4H_9$S—$C_6H_4$ | 206–207 | bluish violet crystal |
| 27 | p-n-$C_3H_7$—$C_6H_4$ | 199–200 | gold crystal |
| 28 | 2,6-$(C_2H_5)_2C_6H_4$ | 180.5–181.5 | gold crystal |
| 29 | 3,5-$(CH_3)_2C_6H_4$ | 259–260 | blackish green crystal |
| 30 | p-$(CH_3$S$)C_6H_4$ | 228–229 | copper-colored crystal |
| 31 | 3,5-$(CH_3$O$)C_6H_4$ | 259–260 | blackish green crystal |
| 32 | o-$(CH_3$O$)C_6H_4$ | 202.1–202.9 | blackish gold crystal |
| 33 | H | ≧300 | gold crystal |
| 34 | $(CH_3)_3$C—OC(=O) | 138.5–140 | blackish green crystal |
| 35 | $CH_2$=CHCH$_2$ | 167–167.5 | bronzy crystal |

Figure 3:
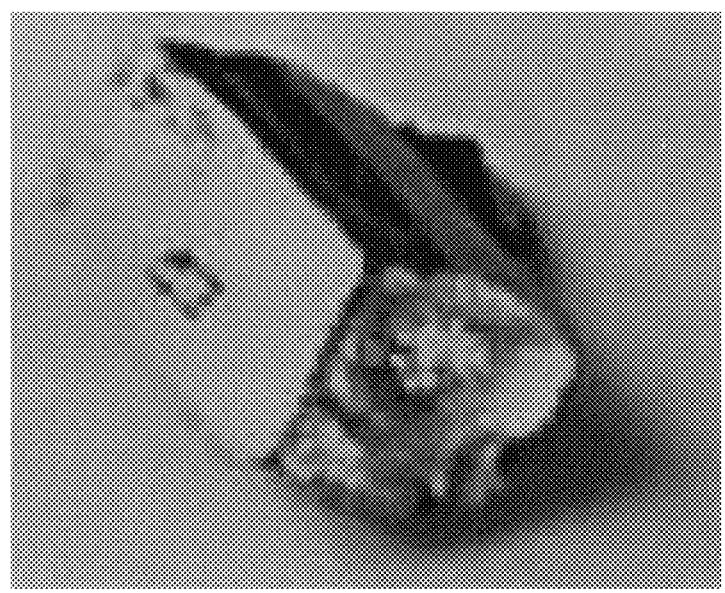
FIG. 3 is a photograph showing the crystal of the compound in Example 27, 1-(4-propylphenyl)-2-(2-thienyl)-5-(5-tricyanoethenyl-2-thienyl)pyrrole.

FIG. 2 is a photograph showing crystals of the compound produced in Example 20, 1-(2-bromophenyl)-2-(2-thienyl)-5-(5-tricyanoethenyl-2-thienyl)pyrrole, and FIG. 3 is a photograph showing crystals of the compound produced in Example 27, 1-(4-n-propylphenyl)-2-(2-thienyl)-5-(5-tricyanoethenyl-2-thienyl)pyrrole.

EXAMPLE 36

Magenta powder of the compound in Example 13, 1-(4-n-dodecylphenyl)-2-(2-thienyl)-5-(5-tricyanoethenyl-2-thienyl)pyrrole was heated to 140–145° C. to melt it, and then cooled it to generate gold colored crystal.

EXAMPLE 37

Figure 4:
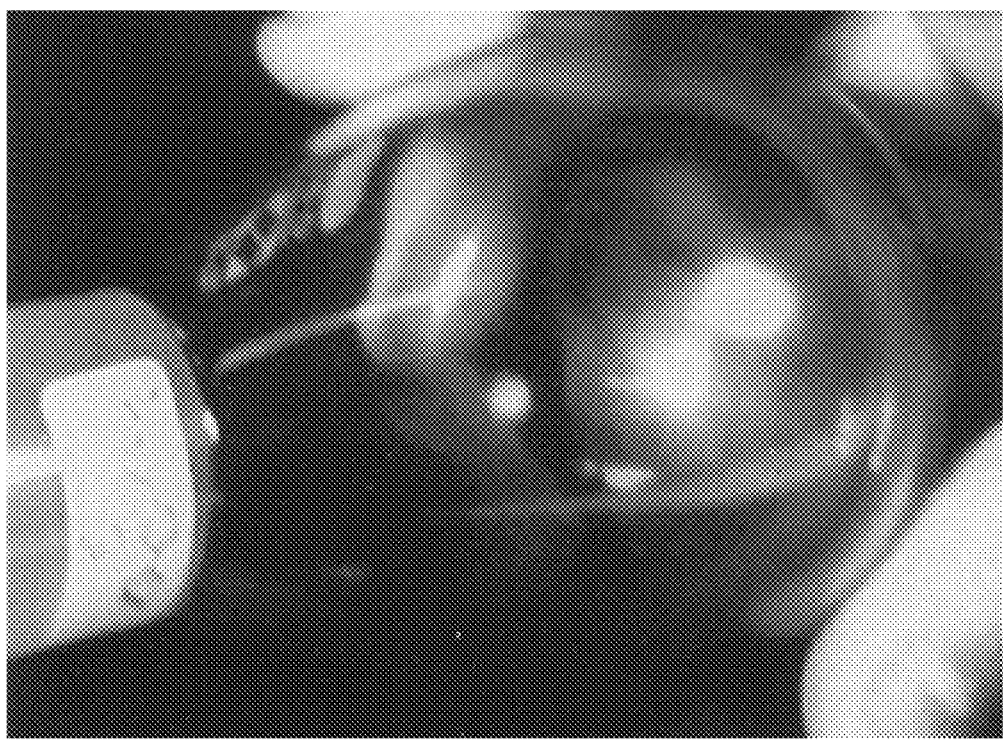
FIG. 4 is a photograph showing a thin film formed from the bronzy crystals of the compound in Example 9, 1-(4-n-butylphenyl)-2-(2-thienyl)-5-(5-tricyanoethenyl-2-thienyl)pyrrole.

A solution of the bronzy crystals of the compound produced in Example 9, 1 -(4-n-butylphenyl)-2-(2-thienyl)-5-(5-tricyanoethenyl-2-thienyl)pyrrole, in chloroform was pored into 200 ml of eggplant type flask. Then the chloroform was evaporated slowly while the flask was rolled. As a result, a bronzy to gold colored thin film was appeared on the inner surface of the bottom of the flask as shown in FIG. 4.

What is claimed is:

1. A pyrrole derivative shown by the following general formula:

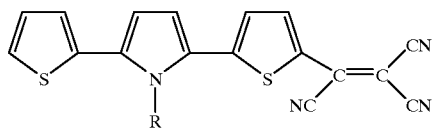

R represents hydrogen, a substituted or unsubstituted alkyl or cycloalkyl group, a substituted or unsubstituted aromatic group, formyl group, an acyl group, an alkoxycarbonyl group, or an alkenyl group.

2. A pyrrole derivative according to claim 1, in which R represents a substituted or unsubstituted alkyl or cycloalkyl group.

3. A pyrrole derivative according to claim 1, in which R represents a substituted or unsubstituted aromatic group.

4. A pyrrole derivative according to claim 1, in which R represents a formyl group.

5. A pyrrole derivative according to claim 1, in which R represents an acyl group.

6. A pyrrole derivative according to claim 1, in which R represents an alkoxycarbonyl group.

7. A pyrrole derivative according to claim 1, in which R represents an alkenyl group.

8. A pyrrole derivative according to claim 1 or 2, in which the alkyl group for R has 1–18 carbons and the cycloalkyl group for R has 3–18 carbons.

9. A pyrrole derivative according to claim 1 or 2, in which the alkyl group for R has 1–12 carbon(s) and the cycloalkyl group for R has 3–12 carbons.

10. A pyrrole derivative according to claim 1 or 2, in which the substituent for the alkyl or cycloalkyl group is an alkoxy group having 1–18 carbon(s).

11. A pyrrole derivative according to claim 1 or 2, in which the substituent for the alkyl or cycloalkyl group is an aromatic group selected from the group consisting of a phenyl group, a naphthyl group, a benzothienyl group, an indolyl group, a pyridyl group, a phenoxy group, and a naphthyloxy group.

12. A pyrrole derivative according to claim 1 or 2, in which the substituent for the alkyl or cycloalkyl group is a halogen atom selected from the group consisting of bromine, iodine, chlorine, and fluorine.

13. A pyrrole derivative according to claim 1 or 3, in which the aromatic group constituting R is a phenyl group, s naphthyl group, a thienyl group, a benzothienyl group an indolyl group, or a pyridyl group.

14. A pyrrole derivative according to claim 1 or 3, in which the substituent for the aromatic group is at least one member selected from the group consisting of an alkyl group having 1–18 carbon(s), an alkoxy group having 1–18 carbon(s), a phenoxy group, a naphthyloxy group, a monoalkylamino group, a dialkylamino group, a thioalkyl group, a bromine atom, an iodine atom, a chlorine atom, and a fluorine atom.

15. A pyrrole derivative according to claim 1 or 3, in which the aromatic group is a substituted aromatic group substituted with a monoalkyl amino group, a dialkyl-amino group or a thioalkyl group and the alkyl moiety of the monoalkylamino group, the dialkylamino group or the thioalkyl group has 1–18 carbon(s).

16. A pyrrole derivative according to claim 1, in which the acyl group, the alkoxycarbonyl group, or the alkenyl group for R has 2–18 carbons.

17. A pyrrole derivative according to claim 1 in the form of a film.

18. A method of preparing the pyrrole derivatives according to claim 1, which comprises the step of reacting a compound shown by the following general formula with tetracyanoethylene;

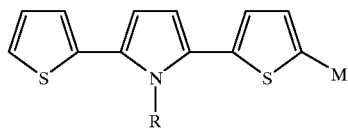

R represents hydrogen, a substituted or unsubstituted alkyl or cycloalkyl group, a substituted or unsubstituted aromatic group, a formyl group, an acyl group, an alkoxycarbonyl group, or an alkenyl group; and M represents a hydrogen atom or a lithium atom.

* * * * *